United States Patent [19]

Kawamura

[11] Patent Number: 5,106,876
[45] Date of Patent: Apr. 21, 1992

[54] WATER-INSOLUBLE HYDROGEL AND METHOD FOR PRODUCTION THEREOF BY USING RADIATION, FREEZING AND THAWING

[75] Inventor: Yasuhiro Kawamura, Hino, Japan

[73] Assignee: Terumo Kabushiki Kaisha, Tokyo, Japan

[21] Appl. No.: 409,755

[22] Filed: Sep. 20, 1989

[30] Foreign Application Priority Data

Sep. 22, 1988 [JP] Japan .................. 63-236470

[51] Int. Cl.⁵ .................. C08F 2/46; C08J 9/38
[52] U.S. Cl. .................. 522/5; 522/86; 521/50.5; 521/52
[58] Field of Search .................. 522/5, 86; 521/50.5, 521/52

[56] References Cited

U.S. PATENT DOCUMENTS

| 4,025,391 | 5/1977 | Kawashima et al. .................. 522/5 |
| 4,734,097 | 3/1988 | Tanabe et al. .................. 524/557 |

FOREIGN PATENT DOCUMENTS

| 58-44699 | 10/1983 | Japan . |
| 128475 | 11/1988 | Japan . |
| 63-292945 | 11/1988 | Japan . |

Primary Examiner—Marion E. McCamish
Assistant Examiner—Mark A. Chapman
Attorney, Agent, or Firm—Burns, Doane, Swecker & Mathis

[57] ABSTRACT

A water-isoluble hydrogel, obtained by cross-linking a polyvinyl alcohol by itself, a polyvinyl pyrrolidone by itself, and a polyvinyl alcohol and a polyvinyl pyrrolidone as a pair by exposure to radiation to a cross-linking degree enough for occlusion therein of 50 to 99% by weight of water and they freezing and thawing the product of said cross-linking, production thereof, and an untrasonic transmission medium using the hydrogel.

33 Claims, 1 Drawing Sheet

WATER-INSOLUBLE HYDROGEL AND METHOD FOR PRODUCTION THEREOF BY USING RADIATION, FREEZING AND THAWING

BACKGROUND OF THE INVENTION

1. Field of the Invention

This invention relates to a water-insoluble hydrogel, a method for the production thereof, and an ultrasonic transmitting medium. More particularly, it relates to a water-insoluble hydrogel having a high water content, permitting easy sterilization, excelling in biocompability, exhibiting high mechanical strength, and producing pleasant tactile sensation, a method for the production thereof, and an ultrasonic transmitting medium using the water-insoluble hydrogel.

2. Description of the Prior Art

For the cardiotomy to be performed precisely on the ailing heart, it is desirable that the patient should be given a deliberate diagnosis prior to the operation for the determination of the position and shape of the morbid region, the relation of the morbid region with the adjoining normal region, and so on. Particularly, in a serious case involving a neonate, this diagnosis constitutes itself an important task which determines the outcome of the operation. The ultrasonic diagnosis has advanced and disseminated remarkably in recent years as a non-invasive testing method applicable to the circulatory region. The accuracy of the preoperative ultrasonic diagnosis is contributing immensely to the improvement of results of recent surgical operations. By the preoperative sonic test carried out by applying a probe on the wall of the chest while avoiding the lungs and the bones, no sufficient information is obtained concerning the cardiac disease and the morbid location. As a way of conducting a more deliberate ultrasonic diagnosis beyond the existing limit, the act of carrying out the ultrasonic test during the course of cardiotomy is conceivable. To be more specific, when the ultrasonic test is carried out after the sternum has been incised mediated and before the pericardium, the heart, or the blood vessel is incised by directly applying the probe on the outside of the organ, a more detailed surgically useful diagnosis is obtained with respect to the lumen of the organ. By this method, it is made possible to confirm during the course of a surgical operation whether or not the surgical treatment being carried out in consequence of the ultrasonic test made during the course of surgical operation is proper. This fact is important for the prevention of repetition of a surgical operation and the postoperative management of the patient.

When the ultrasonic test is carried out by directly applying the probe on the wall of the heart or the blood vessel, the heart or the blood vessel is ununiformly moving in concert with the heartbeat and the pressure of the probe tends to induce arrhythmia or lower the blood pressure. It is, therefore, difficult for the conventional probe possessing an inflexible contact surface to be safely used as incessantly held tightly on the surface of the pulsating heart. In actuality, the usefulness of the real-time ultrasonic laminagraphic testing method performed during the course of a surgical operation is not fully manifested. A suitable substance is required as a contact medium for use in the ultrasonic test during the course of a surgical operation. Specifically, a need is felt for a gel-like elastic substance possessing softness and strength necessary in following the movement of the heart while adhering tightly to the surface and, at the same time, excelling in biocompability and ultrasonic characteristic.

Heretofore, as a material for use in medical devices and implements, a hydrogel having not less than 40% of water contained in a structure produced by occluding polyvinyl pyrrolidone in a cross-linked polyvinyl alcohol type hydrophilic macromolecular network has been known. This hydrogel is obtained by mixing a polyvinyl alcohol type hydrophilic macromolecular substance with polyvinyl pyrrolidone and thereafter insolubilizing only the polyvinyl alcohol type hydrophilic macromolecular moiety of the mixture (Japanese Patent Publication SHO 58(1983)-44,699).

This hydrogel, however, poses as a problem the treatment of the unaltered cross-linking agent such as concentrated sulfuric acid and, moreover, has the disadvantage that it is not easily sterilized, though it excels in biocompability. For example, it offers no sufficient resistance to heat when it is sterilized in an autoclave. When it is sterilized with ethylene oxide gas, since the hydrogel occludes a large amount of water, the ethylene oxide gas is absorbed in the water and suffered to remain therein or part of the absorbed ethylene oxide gas is converted into ethylene glycol and again suffered to remain as such. Owing to the toxicity of the persisting ethylene oxide or ethylene glycol, the hydrogel is not allowed to be sterilized with the ethylene oxide gas. When the hydrogel is sterilized by radiation, the cross-linking proceeds to excess and the reaction of a free radical present in the material gives rise to oxygen, hydrogen peroxide, hydrogen, etc. Thus, the hydrogel which has undergone this sterilization is no longer suitable for the intended use.

As materials for use in such medical devices and implements, we have proposed water-insoluble hydrogels which contain 50 to 99% by weight of water and which are produced by cross-linking two polyvinyl alcohols, two polyvinyl pyrrolidones, and a polyvinyl alcohol and a polyvinyl pyrrolidone by exposure to radiation with a polymerization degree enough for the occlusion of the amount of water mentioned above (Japanese Patent Application SHO 62(1987)-128,475). This water-insoluble hydrogel has a high water content, allows easy sterilization, and excels not only in biocompability but also in acoustic characteristic and, therefore, proves to be useful for such medical implements as ultrasonic transmission medium. It nevertheless has the problem that it has no sufficient physical strength, peels off the skin on exposure to the impact of touch with the clothing, and sustains breakage while in use. Immediately after removal from a wrapper, it is slippery to the touch. The hands used in handling it must be given thorough washing. Thus, a desire has been expressed to improve this hydrogel. It is possible, for example, to enhance the physical strength by increasing the dosage of radiation thereby heightening the cross-link density. This measure, however, degrades the elasticity of the hydrogel and imparts brittleness to it and affects the occurrence of bubbles during the course of reaction. Thus, it can be hardly called a suitable method.

An object of this invention is to provide an improved water-insoluble hydrogel and a method for the production thereof.

Another object of this invention is to provide a water-insoluble hydrogel having a high water content, allowing easy sterilization, excelling in biocompability, exhibiting high physical strength, and producing pleasant tactile sensation and a method for the production thereof.

A further object of this invention is to provide an ultrasonic transmission medium using the hydrogel mentioned above.

SUMMARY OF THE INVENTION

The objects described above are accomplished by a water-insoluble hydrogel which is produced by cross-linking a polyvinyl alcohol by itself, a polyvinyl pyrrolidone by itself, and a polyvinyl alcohol and a polyvinyl pyrrolidone as a pair by exposure to radiation to a cross-linking degree enough for occlusion therein of 50 to 99% by weight, freezing the product of cross-linking, and thawing the frozen product.

This invention discloses a water-insoluble hydrogel having a freezing temperature in the range of $-6°$ to $-120°$ C., preferably $-10°$ to $-60°$ C. This invention further discloses a water-insoluble hydrogel having a freezing time of not less than 15 minutes. This invention also discloses a water-insoluble hydrogel having polyvinyl alcohols and polyvinyl pyrrolidones cross-linked to a cross-linking degree such enough for occlusion therein of 75 to 97% by weight of water. Further, this invention discloses a water-insoluble hydrogel having polyvinyl alcohols and polyvinyl pyrrolidones contained therein in a weight ratio in the range of 10:1 to 1:10, preferably 3: to 1:3.

The objects described above are further accomplished by a method for the production of a water-insoluble hydrogel, characterized by exposing a mixed aqueous solution of a polyvinyl alcohol and a polyvinyl pyrrolidone to radiation thereby cross-linking the polyvinyl alcohol by itself and the polyvinyl pyrrolidones by itself and the polyvinyl alcohol and the polyvinyl pyrrolidone as a pair to a cross-linking degree enough for occlusion therein of 50 to 99% by weight of water, freezing the product of the cross-linking, and thawing the frozen product.

This invention discloses a method for the production of a water-insoluble hydrogel, wherein the radiation is used in a dosage in the range of 0.5 to 6 Mrads, preferably 1 to 2.5 Mrads. This invention further discloses a method for the production of a water-insoluble hydrogel, wherein the radiation is $\gamma$ ray or electron beam, preferably $\gamma$ ray. This invention also discloses a method for the production of a water-insoluble hydrogel, wherein the freezing temperature is in the range of $-6°$ to $-120°$ C., preferably $-10°$ to $-60°$ C. Further, this invention discloses a method for the production of a water-insoluble hydrogel, wherein the freezing time is not less than 15 minutes. This invention also discloses a method for the production of a water-insoluble hydrogel, wherein the polyvinyl alcohols and the polyvinyl pyrrolidones are used in a weight ratio in the range of 10:1 to 1:10, preferably 3:1 to 1:3.

The aforementioned objects are also accomplished by an ultrasonic transmission medium formed of a sheet of a water-insoluble hydrogel, produced by exposing a mixed aqueous solution of a polyvinyl alcohol and a polyvinyl pyrrolidone to radiation thereby cross-linking the polyvinyl alcohol by itself, the polyvinyl pyrrolidones by itself, and the polyvinyl alcohol and the polyvinyl pyrrolidone as a pair to a cross-linking degree enough for occlusion therein of 50 to 99% by weight of water, freezing the product of the cross-linking, and thawing the frozen product.

This invention discloses ultrasonic transmission medium formed of a sheet of a water-insoluble hydrogel, wherein the freezing temperature is in the range of $-6°$ to $-120°$ C., preferably $-10°$ to $-60°$ C. This invention also discloses an ultrasonic transmission medium formed of a sheet of a water-insoluble hydrogel, wherein the freezing time is not less than 15 minutes. Further, this invention discloses an ultrasonic transmission medium formed of a sheet of a water-insoluble hydrogel, wherein the cross-linking degree of the polyvinyl alcohols and the polyvinyl pyrrolidones is such as to effect occlusion therein of 75 to 97% by weight of water. Further, this invention discloses an ultrasonic transmission medium formed of a sheet of a water-insoluble hydrogel, wherein the polyvinyl alcohols and the polyvinyl pyrrolidones are used in a weight ratio in the range of 10:1 to 1:10, preferably 3:1 to 1:3.

EXPLANATION OF THE PREFERRED EMBODIMENT

Figure 1:
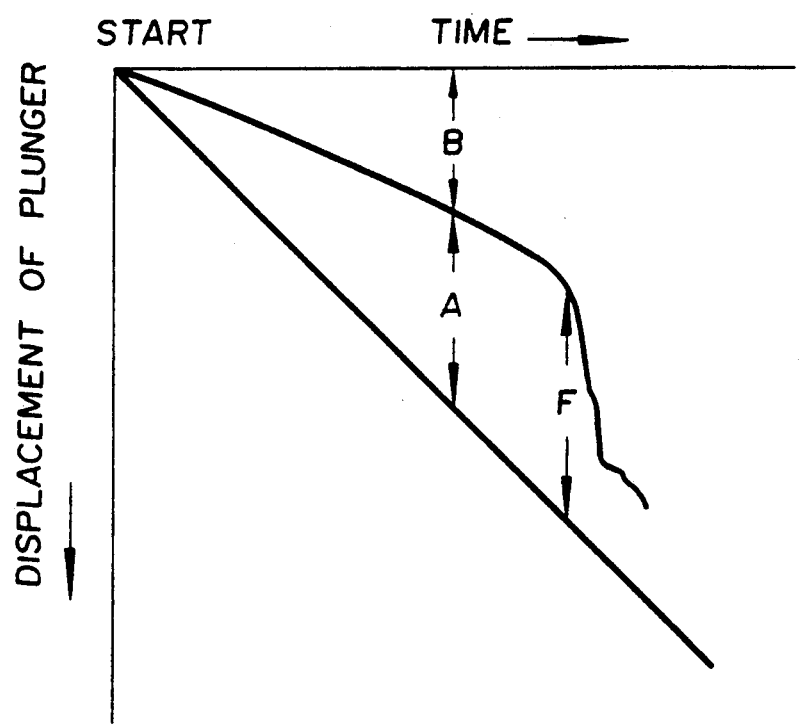
FIG. 1 is a graph for the calculation of gel strength.

The water-insoluble hydrogel of the present invention is produced by cross-linking a polyvinyl alcohol by itself and a polyvinyl pyrrolidones by itself and a polyvinyl alcohol and a polyvinyl pyrrolidone as a pair by exposure to radiation to a cross-linking degree enough for occlusion therein of 50 to 99% by weight of water, then freezing the product of cross-linking, and thawing the frozen product.

When a mixed aqueous solution of a polyvinyl alcohol and a polyvinyl pyrrolidone is exposed to radiation, molecules of a linear polyvinyl alcohol and molecules of a linear polyvinyl pyrrolidone are mutually intertwined uniformly and, at the same time, molecules of the linear polyvinyl alcohol by themselves and molecules of the linear polyvinyl pyrrolidone by themselves and molecules of the linear polyvinyl alcohol and molecules of the linear polyvinyl pyrrolidone are mutually cross-linked to form a reticula structure and this structure is allowed to occlude 50 to 99% by weight of water therein to produce a water-insoluble hydrogel. This statement does not necessarily mean that this water-insoluble hydrogel is regularly cross-linked by the exposure to radiation and that all of the functional groups participate in the cross-linking. Rather, the water-insoluble hydrogel has a small portion thereof cross-linked so as to retain suitable elasticity and, therefore, possesses no sufficient physical strength. Further, water-soluble macromolecules which have escaped participating in the cross-linking and are partially remaining intact leak out of the mass of the water-insoluble hydrogel, presumably to affect the tactile sensation.

In the present invention, the water-insoluble hydrogel obtained as described above is further frozen and then thawed. Incredibly, simply by freezing and then thawing the water-insoluble hydrogel as described above, the water-insoluble hydrogel acquires improved physical strength and tactile sensation without sacrificing viscosity, elasticity, etc. inherent in the hydrogel. Though the exact cause for this improvement remains yet to be elucidated, this improvement may be logically explained by a postulate that the freezing of the hydrogel brings about an enhancement of the crystallinity of the gel texture. It has been known heretofore that the aqueous solution of a polyvinyl alcohol can be gilled by freeze molding the aqueous solution and then thawing the frozen aqueous solution (refer, for example, to Japanese Patent Laid-Open SHO 58(1983)-61,744). The fact that the so-called frozen gel of this kind exhibits conspicuous viscosity and unusual softness has hardly anticipated the improvement of the kind achieved by the present invention.

Now, the present invention will be described more specifically below with reference to embodiments. The polyvinyl alcohols which are usable in this invention include a homopolymer of vinyl acetate, completely saponified copolymer of vinyl acetate with a small proportion (for example, not more than 0.5 mol %, preferably not more than 0.7 mol %) of other copolymerizable vinyl monomer, the product of partial saponification of the same copolymer as mentioned above, and acetal derivatives thereof, for example. The degree of the saponification is in the range of 50 to 100%, preferably 70 to 100%. The degree of polymerization of polyvinyl alcohol is in the range of 50 to 5,000, preferably 1,800 to 2,200. The polyvinyl pyrrolidones which are usable herein include a homopolymer of vinyl pyrrolidone and a copolymer of vinyl pyrrolidone with a small proportion (for example, not more than 0.3 mol %, preferably not more than 0.7 mol %) of other copolymerizable vinyl monomer. The molecular weight of the polyvinyl pyrrolidone is generally in the range of 1,000 to 1,000,000, preferably 2,000 to 460,000. Then, the mixing ratio of a polyvinyl alcohol and a polyvinyl pyrrolidone by weight is in the range of 10:1 to 1:10, preferably 3:1 to 1:3. If the weight ratio is less than 10:1 and the amount of polyvinyl alcohol is small, the produced water-insoluble hydrogel fails to retain sufficient physical properties. Conversely, if this weight ratio exceeds 1:10 and the amount of polyvinyl alcohol is large, the produced water-insoluble hydrogel fails to retain sufficient physical properties.

The production of the water-insoluble hydrogel of the present invention is attained by first dissolving the aforementioned polyvinyl alcohol and vinyl pyrrolidone in water thereby preparing a mixed aqueous solution, placing the mixed aqueous solution in a prescribed molding die, and exposing the solution in the molding die to radiation thereby causing molecules of a linear polyvinyl alcohol and molecules of a linear polyvinyl pyrrolidone to be uniformly intertwined and, at the same time, causing molecules of the linear polyvinyl alcohol by themselves and molecules of the linear polyvinyl pyrrolidone by themselves and these two pairs of molecules mutually to be cross-linked to form a reticula structure and allowing this structure to occlude therein 50 to 99% by weight of water to give rise to a water-insoluble hydrogel.

The water to be used in this case is preferably deionized water or distilled water which has been neutralized with an alkali hydroxide such as sodium hydroxide or potassium hydroxide to a pH value in the range of 6.0 to 8.0. The neutralization serves the purpose of precluding the otherwise possible occurrence of bubbles due to carbon dioxide gas naturally contained in the distilled water or deionized water. This preclusion may be logically explained by a supposition that macromolecules are electrically charged by the alkali ion and are cross-linked in their extended state and are consequently inhibited from including therein the internally generated bubbles.

The molding dies which are usable herein include those made of metals, synthetic resins, ceramics, and glass, for example. The aforementioned mixed aqueous solution may be directly supplied to the molding die and then exposed to radiation. It is allowable otherwise to place the aforementioned mixed aqueous solution in a wrapper made of synthetic resin or aluminum foil and expose the wrapper containing the solution to radiation as held inside the aforementioned molding die or suitably placed elsewhere. The polymer component concentration in the aforementioned mixed solution is in the range of 50 to 1% by weight, preferably 25 to 3% by weight.

The radiations which are usable herein include $\gamma$ ray and electron beam. This invention prefers the $\gamma$ ray to the electron beam in the sense that this radiation enables cross-linking and sterilization to be effected simultaneously. The dosage of the radiation is in the range of 0.5 to 6 Mrads, preferably 1 to 2.5 Mrads. Particularly when the exposure to the radiation is carried out with the mixed aqueous solution held in the wrapper as mentioned above, there is obtained the water-insoluble hydrogel contained in the wrapper which has undergone cross-linking and sterilization at the same time. This procedure proves to be highly convenient from the standpoint of handling. At the time of use, by merely opening the wrapper, the water-insoluble hydrogel is readied in a sterilized state for use. The reason for limiting the dosage of the radiation to the range of 0.5 to 6 Mrads is that the water-insoluble hydrogel has no sufficiently high polymerization degree and consequently fails to retain its own shape if the dosage is less than 0.5 Mrad and the water-insoluble hydrogel has unduly high hardness and exhibits poor tight adhesiveness to the contour of the skin under treatment if the dosage exceeds 6 Mrads. The cross-linking degree in this case is such as to permit occlusion of 50 to 99% by weight, preferably 75 to 97% by weight, of water in the production water-insoluble hydrogel.

In the method of this invention for the production of a water-insoluble hydrogel, the water-insoluble hydrogel to be obtained in consequence of the exposure to the radiation effected as described above is further subjected to a step of freezing and thawing.

The freezing temperature of the water-insoluble hydrogel suitably is aporoximately in the range of $-6°$ to $-120°$ C., preferably $-10°$ to $-60°$ C. The reason for this range is that the improvement of physical strength and tactile sensation is not sufficiently obtained if the freezing temperature is higher than $-6°$ C. and the freezing operation proves to be uneconomical if the freezing temperature is lower than $-120°$ C. The freezing time is preferability not less than 15 minutes roughly on the condition that the freezing temperature is in the range of $-6°$ to $-120°$ C. The reason for this lower limit is that the produced hydrogel acquires no sufficient improvement in physical strength and tactile sensation if the freezing time is unduly short and the produced hydrogel acquires an extremely large hydrogen bond content possibly to an extent of impairing the softness of the hydrogel.

When a sheet of the water-insoluble hydrogel is to be used as an ultrasonic transmission medium, the thickness of this sheet is in the range of 1 to 70 mm, preferably 5 to 50 mm.

The water-insoluble hydrogel of this invention obtained as described above can be used as an ultrasonic transmission medium such as, for example, an ultrasonic mat in an ultrasonic diagnostic device in the place of an ultrasonic gel liable to impart unpleasant feeling on a patient under treatment or a material for the same device to be employed in the in-operation diagnosis which is currently under a devoted research. It can be used also as medical materials such as a carrier for gradual release drug or as a membrane for the prevention of intestinal conglutination. When the water-insoluble hydrogel of this invention is used in an ultrasonic diagnostic device, the use of the device is not limited to the in-operation diagnosis. When it is placed on the surface of a patient's body, it precludes the otherwise possible deformation of tissue under the pressure of a probe and allows morphological diagnosis to be carried out accurately. Further, when a region at a relatively small depth in a patients body is to be observed with a low frequency (3.5 MHz or 5 MHz, for example), an image of the region is obtained with high resolution by interposing the water-insoluble hydrogel of a prescribed thickness between the probe and the surface of the body and moving the focal point to the shallow part of the body. Thus, the ultrasonic transmission medium of this invention is suitable for a wide variety of kinds of diagnosis. The water content mentioned in the present specification is used on the basis of the following definition.

$$\text{Water content} = \frac{\text{(Weight of hydrated macromolecules)} - \text{(Absolute weight of macromolecules)}}{\text{Weight of hydrated macromolecules}} \times 100 \, (\%)$$

Now, the method of this invention will be described more specifically below with reference to working examples.

EXAMPLE 1

In 160 ml of deionized water adjusted in advance to pH 7.0 by addition of sodium hydroxide, 6 g of polyvinyl alcohol (polymerization degree 2,000 and saponification degree 95%) and 9.2 g of polyvinyl pyrrolidone [(K30) molecular weight 40,000] were stirred and dissolved at a temperature in the range of 80° to 90° C. The resultant aqueous solution was cooled to room temperature. This aqueous solution was placed in a bag made of polyethylene sheet and exposed to 2.25 Mrads of γ ray, to produce a sheet of water-insoluble hydrogel 5 mm in thickness. This hydrogel was found to contain absolutely no bubble.

Then, this water-insoluble hydrogel was cooled to −20° C., left freezing at this temperature for 6 hours, and then thawed, to afford a final product.

The finally produced water-insoluble hydrogel was tested for water content, gel hardness, gel strength at rupture, and tactile sensation. The results were as shown in Table 1.

The data on gel hardness and gel strength at rupture shown in Table 1 were obtained by the use of a tester produced by Iio Denki K. K. and marketed under trademark designation of Neocard Meter type M-302. Specifically, a load was applied to a sample in the tester to measure the displacement of a plunger as the function of time and the results of this measurement were plotted in a graph shown in FIG. 1. The magnitudes in question were calculated from the following formulas, using the values of A, B, and F read out of the graph.

$$\text{Gel Hardness} = \frac{A}{B} \times \frac{65.33}{2\pi\tau} \, W \times \frac{1}{980} \, (\text{g/cm}^2)$$

$$\text{Gel strength at rupture} = \frac{F}{\pi\tau^2} \times \frac{W}{100} \, (\text{g/cm}^2)$$

wherein r is the radius of the plunger (cm) and W is the load (g) and 65.33 is the spring constant (dyne/cm). The tactile sensation indicated in Table 1 represents the data obtained by causing a panel of subjects to touch the sample directly with their hands, report their feeling of the touch, and analyzing the contents of the report.

A sheet of the water-insoluble hydrogel was interposed between a probe of a ultrasonic diagnosis device (Sonic Scanner TS-100, produced by Terumo K. K.) and the region under examination and tested for basic acoustic characteristic. The results were as shown in Table 2.

Control 1

A water-insoluble hydrogel was obtained by repeating the procedure of Example 1, except that the treatment of freezing and thawing was omitted. This water-insoluble hydrogel was tested for water content, gel hardness, gel strength at rupture, and tactile sensation in the same manner as in Example 1. The results were as shown in Table 1. A sheet of this water-insoluble hydrogel was tested for basic acoustic characteristic similarly to example 1. The results were as shown in Table 2.

TABLE 1

|  | Gel Strength (g/cm2) | Gel hardness (g/cm2) | Water content (% by weight) | Tactile sensation |
| --- | --- | --- | --- | --- |
| Example 1 | 1950 | 150 | 91.3 | No slippery sensation |
| Control 1 | 1460 | 130 | 91.3 | Slippery Sensation produced |

TABLE 2

|  | Temperature during test (°C.) | Ratio of attenuation (dB/cm) | Sonic velocity (m/s) |
| --- | --- | --- | --- |
| Example 1 | 23.5 | 0.70 | 1530 |
|  | 22.0 | 0.65 | 1530 |
| Control 1 | 23.5 | 0.72 | 1530 |
|  | 22.0 | 0.68 | 1530 |

It is clearly noted from Table 1 and Table 2 that the water-insoluble hydrogel of this invention (Example 1) was observed to acquire improved strength at rupture and tactile sensation without any substantial variation in water content, elasticity, acoustic characteristic, etc. as compared with the water-insoluble hydrogel which escaped the treatment of freezing and thawing.

As described above, this invention concerns a water-insoluble hydrogel obtained by cross-linking a polyvinyl alcohol by itself and a polyvinyl pyrrolidone by itself and a polyvinyl alcohol and a polyvinyl pyrrolidone as a pair by exposure to radiation to a cross-linking degree enough for occlusion therein of 50 to 90% by weight of water and then freezing and thawing the product of cross-linking. Thus, this water-insoluble hydrogel possesses high physical strength, excels in tactile sensation, allows high ease of handling, possesses a high water content, permits easy sterilization, and excels not only in bioadaptability but also in acoustic characteristic. Owing to these strong points, the water-insoluble hydrogel manifests an outstanding effect as an ultrasonic transmission medium usable typically in the form of an ultrasonic mat.

The method of this invention for the production of a water-insoluble hydrogel is characterized by exposing a mixed aqueous solution of a polyvinyl alcohol and a polyvinyl pyrrolidone to radiation thereby cross-linking the polyvinyl alcohol by itself and the polyvinyl pyrrolidone by itself and the polyvinyl alcohol and the polyvinyl pyrrolidone as a pair to a cross-linking degree enough for occlusion therein of 50 to 99% by weight of water and then freezing and thawing the product of the cross-linking. Thus, the aforementioned improvement of the water-insoluble hydrogel in physical strength and tactile sensation owing to the exposure to radiation is attained by the addition of a very simple step. This method is perfectly free from the problem that the unaltered cross-linking agent remains in the final product. Particularly when the γ ray is used for the exposure, since cross-linking and sterilization are simultaneously attained, the process of operation can be simplified and the product can be obtained with consistent quality.

What is claimed is:

1. A water-insoluble hydrogel, obtained by cross-linking a polyvinyl alcohol by itself, a polyvinyl pyrrolidone by itself, and a polyvinyl alcohol and a polyvinyl pyrrolidone as a pair by exposure to radiation to a cross-linking degree enough for occlusion therein of 50 to 99% by weight of water and then freezing and thawing the product of said cross-linking.

2. A water-insoluble hydrogel according to claim 1, wherein the dosage of radiation is in the range of 0.5 to 6 Mrads.

3. A water-insoluble hydrogel according to claim 2, wherein said radiation is γ ray.

4. A water-insoluble hydrogel according to claim 1, wherein the freezing temperature is in the range of −6° to −120° C.

5. A water-insoluble hydrogel according to claim 1, wherein said polyvinyl alcohol and said polyvinyl pyrrolidone are used in a weight ratio in the range of 10:1 to 1:10.

6. A water-insoluble hydrogel according to claim 2, wherein said polyvinyl alcohol and said polyvinyl pyrrolidone are used in a weight ratio in the range of 3:1 to 1:3.

7. A water-insoluble hydrogel according to claim 1, wherein the saponification degree of said polyvinyl alcohol is in the range of 50 to 100%.

8. A water-insoluble hydrogel according to claim 7, wherein the polymerization degree of said polyvinyl alcohol is in the range of 50 to 5,000 and the molecular weight of said polyvinyl pyrrolidone is in the range of 1,000 to 1,000,000.

9. A water-insoluble hydrogel according to claim 1, wherein the amount of water to be occluded is in the range of 75 to 97% by weight.

10. A method for the production of a water-insoluble hydrogel, comprising exposing a mixed aqueous solution of a polyvinyl alcohol and a polyvinyl pyrrolidone by exposure to radiation thereby cross-linking said polyvinyl alcohol by itself and said polyvinyl pyrrolidone by itself and said polyvinyl alcohol and said polyvinyl pyrrolidone as a pair to a cross-linking degree for occlusion therein of 50 to 99% by weight of water, and then freezing and thawing the product of said cross-linking.

11. A method according to claim 10, wherein the dosage of radiation is in the range of 0.5 to 6 Mrads.

12. A method according to claim 10, wherein said radiation is γ ray.

13. A method according to claim 10, wherein the freezing temperature is in the range of −6° to −120° C.

14. A method according to claim 10, wherein the freezing time is not less than 15 minutes.

15. A method according to claim 10, wherein the water is put to use after the pH value thereof has been adjusted with an alkali hydroxide to a range of 6.0 to 8.0.

16. A method according to claim 10, wherein said polyvinyl alcohol and said polyvinyl pyrrolidone are used in a weight ratio in the range of 10:1 to 1:10.

17. A method according to claim 11, wherein said polyvinyl alcohol and said polyvinyl pyrrolidone are used in a weight ratio in the range of 3:1 to 1:3.

18. A method according to claim 17, wherein the polymerization degree of said polyvinyl alcohol is in the range of 50 to 5,000 and the molecular weight of said polyvinyl pyrrolidone is in the range of 1,000 to 1,000,000.

19. A method according to claim 10, wherein the amount of water to be occluded is in the range of 75 to 97% by weight.

20. An ultrasonic transmission medium formed of a sheet of a water-insoluble hydrogel obtained by cross-linking a polyvinyl alcohol by itself, a polyvinyl pyrrolidone by itself, and a polyvinyl alcohol and a polyvinyl pyrrolidone as a pair by exposure to radiation to a cross-linking degree enough for occlusion therein of 50 to 99% by weight of water and then freezing and thawing the product of said cross-linking.

21. A medium according to claim 20, wherein the dosage of radiation is in the range of 0.5 to 6 Mrads.

22. A medium according to claim 21, wherein said radiation is γ ray.

23. A medium according to claim 21, wherein said polyvinyl alcohol and said polyvinyl pyrrolidone are used in a weight ratio in the range of 3:1 to 1:3.

24. A medium according to claim 20, wherein the freezing temperature is in the range of −6° to −120° C.

25. A medium according to claim 20, wherein said radiation is γ ray.

26. A medium according to claim 20, wherein the saponification degree of said polyvinyl alcohol is in the range of 50 to 100%.

27. A medium according to claim 20, wherein the saponification degree of said polyvinyl alcohol is in the range of 70 to 100%.

28. A medium according to claim 20, wherein the amount of water to be occluded is in the range of 75 to 97% by weight.

29. A medium according to claim 20, wherein the thickness of said sheet is in the range of 1 to 70 mm.

30. A method of ultrasonic diagnosis comprising using an ultrasonic transmission medium formed of a sheet of a water-insoluble hydrogel obtained by cross-linking a polyvinyl alcohol by itself, a polyvinyl pyrrolidone by itself, and a polyvinyl alcohol and a polyvinyl pyrrolidone as a pair by exposure to radiation to a cross-linking degree enough for occlusion therein of 50 to 99% by weight of water and then freezing and thawing the product of said cross-linking.

31. A method according to claim 30, wherein the dosage of radiation is in the range of 0.5 to 6M rads.

32. The method according to claim 30, wherein said radiation is τ ray.

33. The method according to claim 30, wherein the freezing temperature is in the range of −6° to −120° C.

* * * * *